(12) United States Patent
Baynham et al.

(10) Patent No.: US 6,224,599 B1
(45) Date of Patent: May 1, 2001

(54) VIEWABLE WEDGE DISTRACTOR DEVICE

(76) Inventors: Matthew G. Baynham, 8049 Monetary Dr., Unit 5C, Riviera Beach, FL (US) 33404; G. Clay Baynham, Eight Eastwinds Cir., Tequesta, FL (US) 33460

( * ) Notice: Subject to any disclaimer, the term of this patent is extended or adjusted under 35 U.S.C. 154(b) by 0 days.

(21) Appl. No.: 09/517,469

(22) Filed: Mar. 2, 2000

Related U.S. Application Data

(60) Provisional application No. 60/134,924, filed on May 19, 1999.

(51) Int. Cl.[7] .................................................... A61B 17/70
(52) U.S. Cl. ................................ 606/61; 606/79; 606/99
(58) Field of Search ................................ 606/60, 61, 79, 606/90, 96, 99, 102, 105; 623/17.11, 17.16

(56) References Cited

U.S. PATENT DOCUMENTS

| 5,306,309 | 4/1994 | Wagner et al. . |
| 5,425,772 | 6/1995 | Brantigan . |
| 5,683,464 | 11/1997 | Wagner et al. . |
| 5,722,977 | 3/1998 | Wilhelmy . |
| 5,766,252 | 6/1998 | Henry et al. . |
| 5,797,909 | * 8/1998 | Michelson .............................. 606/61 |
| 5,893,890 | 4/1999 | Pisharodi . |
| 5,968,098 | * 10/1999 | Winslow ........................... 623/17.11 |
| 6,042,582 | * 3/2000 | Ray ........................................ 606/61 |
| 6,113,602 | * 9/2000 | Sand ...................................... 606/61 |

* cited by examiner

Primary Examiner—David O. Reip
(74) Attorney, Agent, or Firm—McHale & Slavin

(57) ABSTRACT

The present invention describes a system comprised of a wedge, distractor channel, and a retractor. The wedge and distractor channel are combined in a nesting relationship and an impactor handle is then attached to the wedge/distractor channel combination to facilitate intervertebral positioning. Subsequent to insertion, the wedge is slidably disengaged while leaving the distractor channel in place, thereby forming an access port which provides an enhanced field of view of the interior spinal anatomy. A retractor is positioned in the incision allowing unobstructed view from outside the body to the access port and facilitates performance of such surgical procedures as discectomy, implant sizing and insertion, spinal fusion, and the like.

11 Claims, 4 Drawing Sheets

VIEWABLE WEDGE DISTRACTOR DEVICE

This application claims benefit to Provisional application 60/134,924 filed May, 19, 1999.

FIELD OF THE INVENTION

This invention relates to a device useful in the performance of spinal surgeries and the process for their use; and particularly relates to a system for distracting the intervertebral space to enable viewing of the spinal column and insertion of an appropriate spacing apparatus.

BACKGROUND OF THE INVENTION

The spine is a column of vertebrae divided into three sections (cervical, thoracic and lumbar). The vertebrae are separated by small cartilaginous cushions identified as intervertebral discs which contain a jelly-like substance called the nucleus pulposus. Additionally, each vertebrae contains several bony projections known as processes which attach to adjacent muscles. These processes interlock at areas termed facet joints and, in concert with the surrounding attached muscles, allow the spine to twist or bend.

When abnormalities such as disc herniation, spinal stenosis, spinal degeneration, cauda equina syndrome, or the like occur in an individual, nerves within or adjacent to the spinal column may become inflamed or impinged resulting in the individual experiencing various forms of pain, loss of flexibility, loss of motion, and possibly loss of bladder and/or bowel control. Additionally, these abnormalities may result in the development of spondylolisthesis, a condition in which one vertebrae slips forward over another.

Although conservative treatments are most often recommended, certain types of injuries, or conditions which result in intractable pain and the possibility of permanent loss of mobility often must be treated surgically.

Typical surgical procedures such as discectomy, laminectomy, and spinal fusion require the surgeon to first gain access to the interior of the spinal column and to the interior faces of the bony processes using either an anterior or posterior approach.

DESCRIPTION OF THE PRIOR ART

U.S. Pat. No. 5,306,309 discloses a spinal disk implant that is inserted by the use of a handle depicted in FIG. 14. The handle has a formed front end for engagement of the implant and may be struck by a hammer if necessary to urge the implant into position.

U.S. Pat. No. 5,425,772 discloses an implant device which employs an insertion tool, not shown, which couples to the implant and allows for placement between adjoining vertebrae.

U.S. Pat. No. 5,683,464 is similar to U.S. Pat. No. 5,306,309 and includes a new style of insertion tool as depicted in FIG. 15. This implant tool includes a pair of flexible opposing arms and a means for securing the implant in place on the delivery tool until properly positioned.

U.S. Pat. No. 5,722,977 discloses a device for removal of vertebrae bone tissue by use of a mortising cutter for harvesting a bone plug from a donor and then inserting the plug into a prepared vertebrae recess.

U.S. Pat. No. 5,766,252 discloses a spinal implant having a wedge shape. The implant is inserted by a handle that couples to the implant.

U.S. Pat. No. 5,893,890 illustrates a vertebrae disk stabilizer. This invention includes a wedge shaped insertion mechanism that allows for the spreading of vertebrae and the insertion of a spinal implant. This invention requires the use of a key way formed integral to the insertion device.

The prior art fails to provide a device or process capable of accessing the internal regions of the spinal column and bony processes without damaging the end plates of adjacent vertebrae.

The present invention teaches a device and a process for its use which enables distraction of the disk space, and provides an enhanced view of the interior area subsequent to insertion without the need for excision of the vertebral end plates, thereby satisfying a long-felt need in the art.

SUMMARY OF THE INVENTION

The present invention describes a system comprised of a wedge and distractor channel constructed from titanium or a titanium alloy. The wedge is constructed and arranged to fit within the distractor channel, and is thus positioned prior to insertion. An appropriately sized combination of wedge and distractor channel are chosen dependent upon the particular anatomical results sought and an impactor handle is then attached to the wedge/distractor channel combination to facilitate insertion between two vertebrae, without trauma to their end plates. The wedge is then extracted, leaving the distractor channel defining means in place for maintenance of the desired degree of distraction and vertebral alignment, and for creation of an access port. The access port allows the surgeon easy ingress to the spinal column and associated anatomical structures. Discectomy is facilitated, as is the insertion of allografts or titanium cages for spinal fusion procedures. When it is desired, decortication means in the form of cutting edges may be incorporated in the wedge structure for abrading the bone adjacent the graft material to accelerate fusion.

Accordingly, it is an objective of the instant invention to teach a device which provides an enhanced view of the interior anatomy of the spine upon insertion.

It is also an objective of the instant invention to teach a retractor in communication with the access port for providing a clear field of view of the interior anatomy of the spine.

It is a further objective of the instant invention to teach a method and device for creation of an access port useful for retrieval of bony abnormalities and/or herneated disk fragments, or the like related spinal procedures which require access to the intervertebral area and surrounding anatomical structures.

It is yet another objective of the instant invention to teach a set of components which enables either an anterior or posterior approach for distraction of the spinous processes and access thereto.

It is a still further objective of the invention to teach a device for partial decortication of the end-plates upon insertion.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
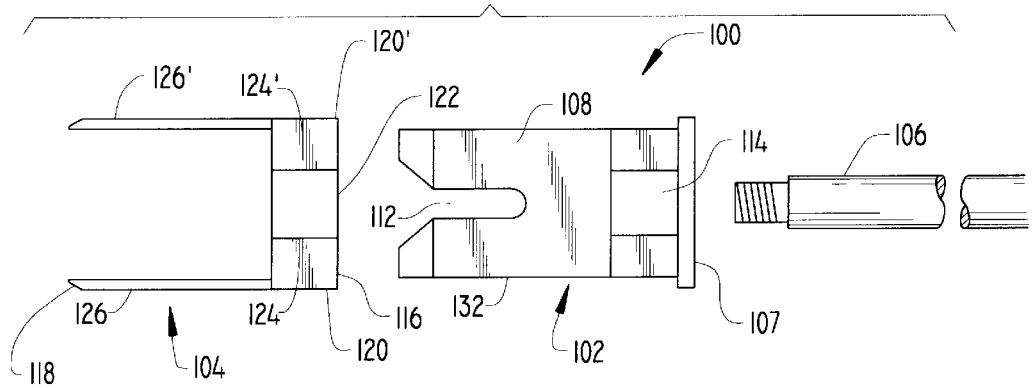
FIG. 1 is an exploded top-view of a combined wedge-channel device.

FIG. 1 is an exploded top-view of the components of a combined wedge-distractor channel device generally referred to as 100 wherein wedge 102 is adapted for insertion within channel defining means 104 and impactor handle 106 is releasably coupled with wedge 102 at impact surface 107. Wedge 102 includes upper and lower surfaces 108 and 110 (FIG. 2), a centrally disposed passage 112 effective for protecting underlying tissues while urging the wedge within an intervertebral space and an upraised portion 114 for maintaining the wedge in rigid engagement with channel defining means 104. In practice, a set of multiple wedge-channel devices are provided in varying sizes from which the surgeon may select an instrument which is appropriately sized for the task at hand. Channel defining means 104 includes a proximal end 116 and a distal end 118, said proximal end including a pair of substantially parallel endwalls 120, 120' spaced apart by a basewall 122 extending therebetween, and a pair of enclosing walls 124, 124' disposed substantially perpendicular to said endwalls and in spaced relation to said basewall. The channel defining means distal end 118 includes wedge-shaped wall members 126, 126' extending from said proximal end and further includes pairs of coplanar edges in converging relationship 128, 130 and 128', 130', defining one or more angles of convergence. The edges are effective to maintain a particular intervertebral space after slidable disengagement of wedge 102, thereby defining a convenient access port within the intervertebral space.

Figure 2:
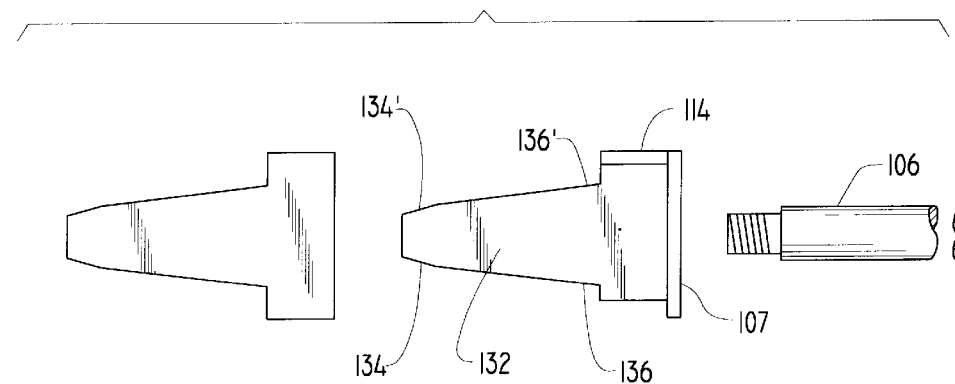
FIG. 2 is an exploded side-view of a combined wedge channel device.

Now referring to FIG. 2, a side view of the combined wedge-distractor channel device generally referred to as 100 is illustrated. This view further illustrates wedge 102 as including wedge shaped side surfaces 132, 132' which have a first convergence angle defined by edges 134, 134' and a second convergence angle defined by edges 136, 136'. This allows for a lesser degree of force to initially distract the intervertebral space along edges 134, 134'. As the device enters the intervertebral space, pressure is distributed across a greater area and an increased amount of force may be exerted.

Figure 3:
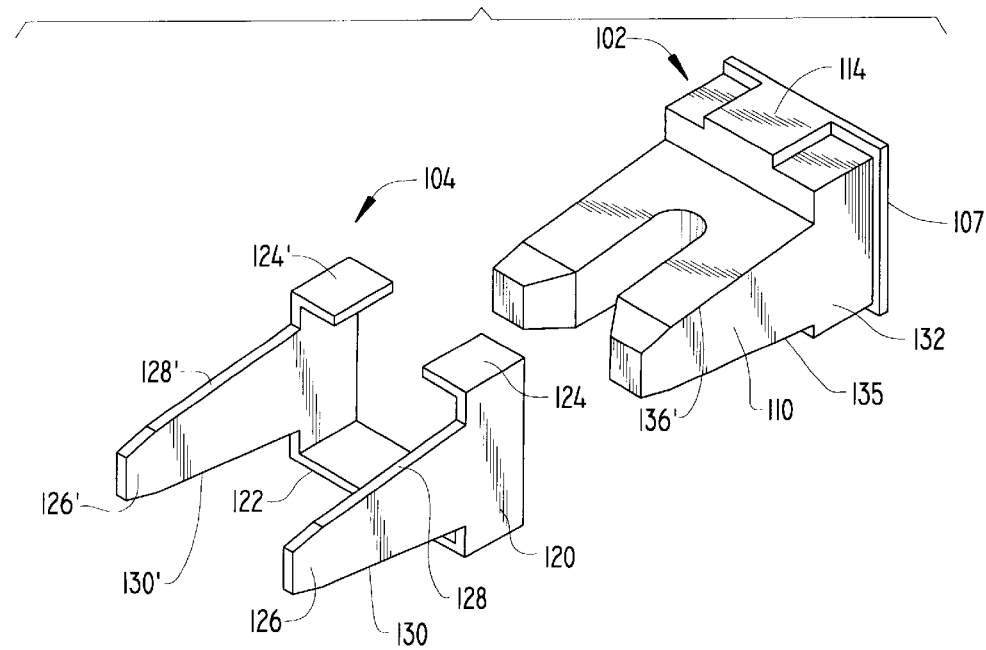
FIG. 3 is a perspective view of an unassembled wedge and channel.

FIG. 3 illustrates a perspective view of the wedge 102 disengaged from channel defining means 104.

Figure 4:
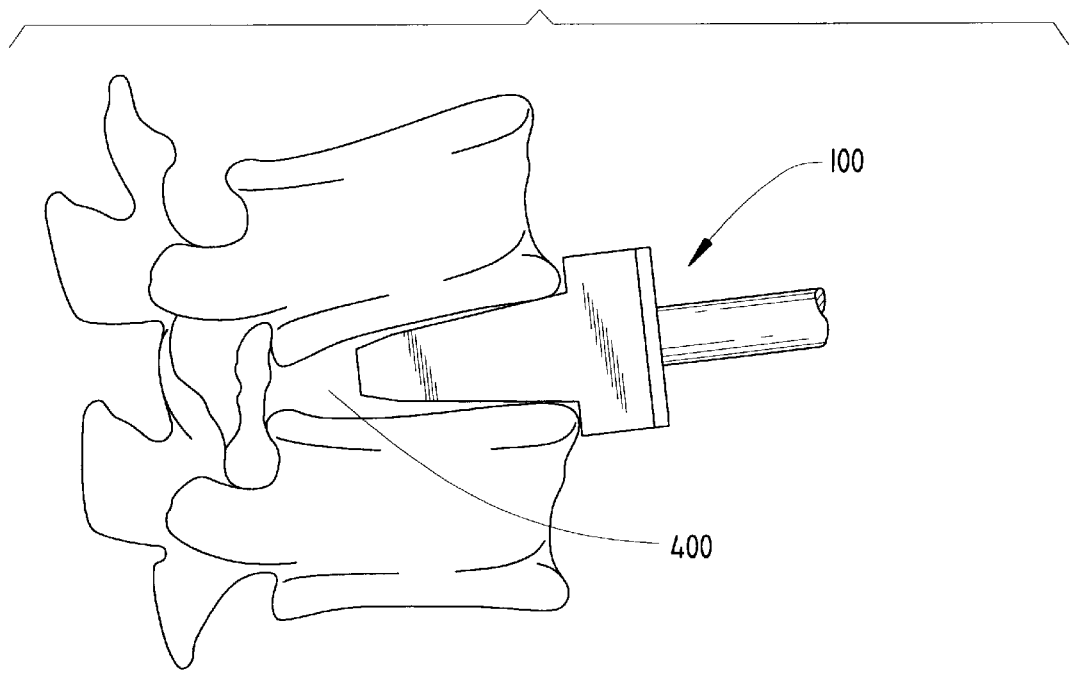
FIG. 4 is a pictorial view of the wedge-channel device inserted within an intervertebral space.
Figure 4:
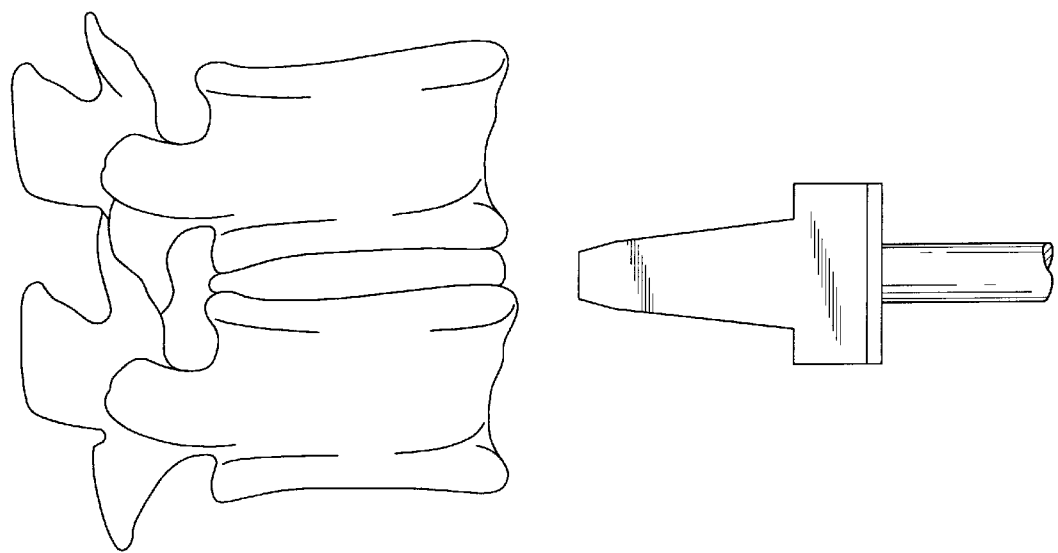

FIG. 4 is a cross sectional view of the wedge-distractor channel device 100 inserted within and intervertebral space 400.

Figure 5:
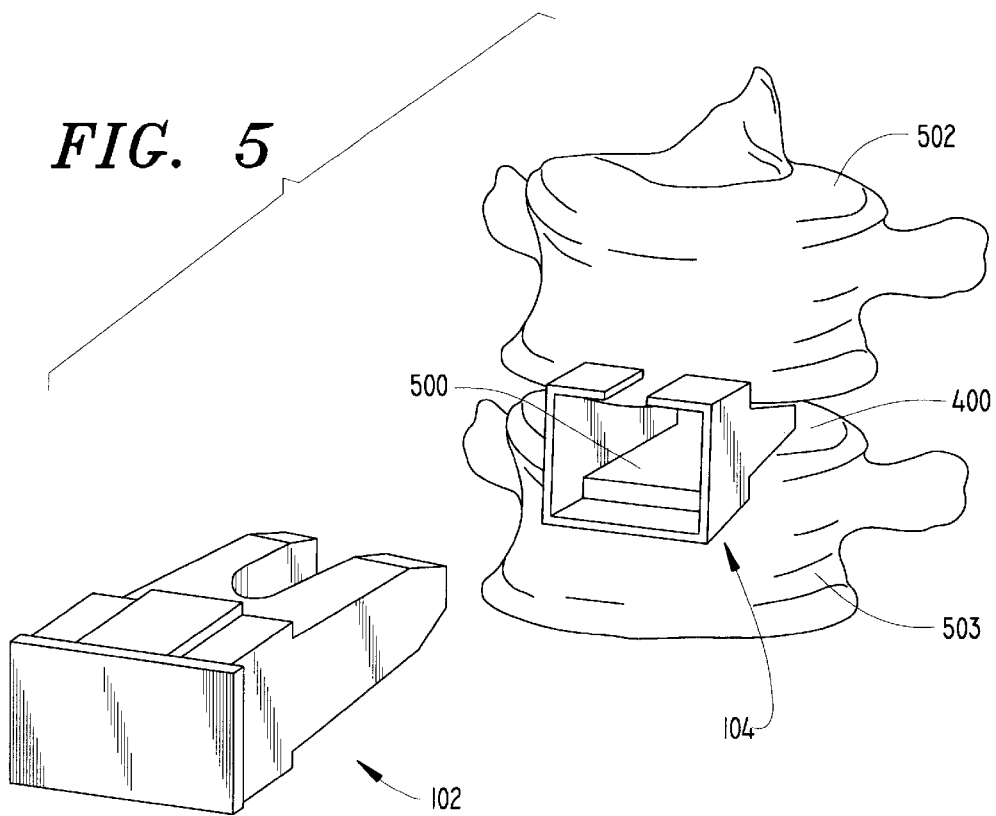
FIG. 5 is a pictorial view of an intervertebrally positioned channel defining an access port subsequent to wedge removal.

FIG. 5 shows a post insertion view of adjacent vertebrae 502 and 503, wherein subsequent to insertion of the assembled wedge-distractor channel device 100 (as depicted in FIG. 4) the wedge 102 is slidably disengaged from the channel defining means 104, resulting in the creation of an access port 500. Various surgical procedures are facilitated by formation of this means of easy ingress and egress.

Figure 6:
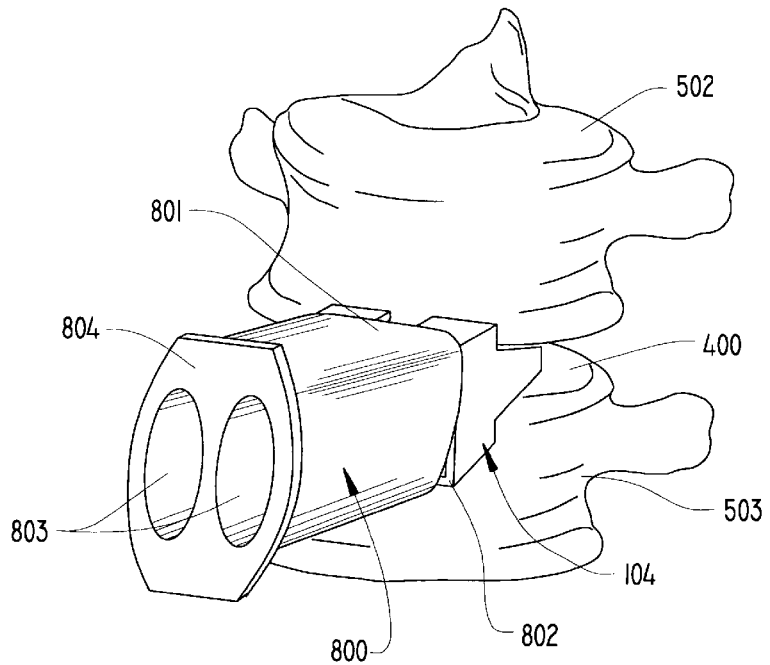
FIG. 6 is a perspective view of a retractor and an intervertebrally positioned channel of FIG. 5.

FIG. 6 shows the channel defining means 104 in place between the vertebrae 502 and 503. The retractor 800 has a smooth distal end (not shown) which is in intimate contact with the proximal end 116 of the channel defining means 104. The retractor 800 is mated to the proximal end 116 of the channel defining means 104 by flanges 801 and 802. The flanges are extensions of the smooth distal end and define a groove through the end of the retractor. The walls of the groove are spaced apart a distance which closely approximates the dimensions of the proximal end 116. This allows the retractor to be positively connected with the channel defining means so that it will not be accidently displaced during the procedure.

As shown, the retractor 800 is somewhat oval shaped to more easily comply with the surgical opening through the tissues of the body. However, other shapes could be used without deleterious results. The retractor prevents the soft tissues about the edges of the incision from interfering with the surgeon's view and instruments. The soft tissues of the body and the flanges 801 and 802 provide stability to the retractor.

The retractor could have one large passageway or more than two passageways in other embodiments. In the preferred embodiment, the retractor 800 has two passageways 803 from end to end. These passageways may be used for various purposes during the operation. For example, the surgeon can utilize one passage for view of the operative field and, simultaneously, use the other passageway for manipulation of surgical instruments. The passageways could also be used for suction and/or lavage. The proximal end of the retractor may be formed with a continuous flange 804 which would contact the patient about the incision further stabilizing the assembly.

Figure 7:
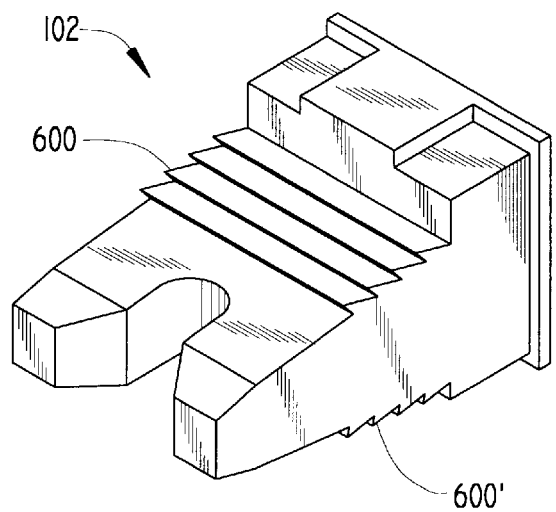
FIG. 7 is a perspective view of a wedge and channel including decorticating surfaces.

FIG. 7 shows a particular embodiment of wedge 102 wherein cascading ridges are provided for decortication in the form of cutting edges 600, 600'. These ridges are provided on the wedges upper and lower surfaces for decortication of the vertebrae to enhance the progress of fusion between the bone and various graft materials, e.g. allografts and titanium or the like.

Figure 8:
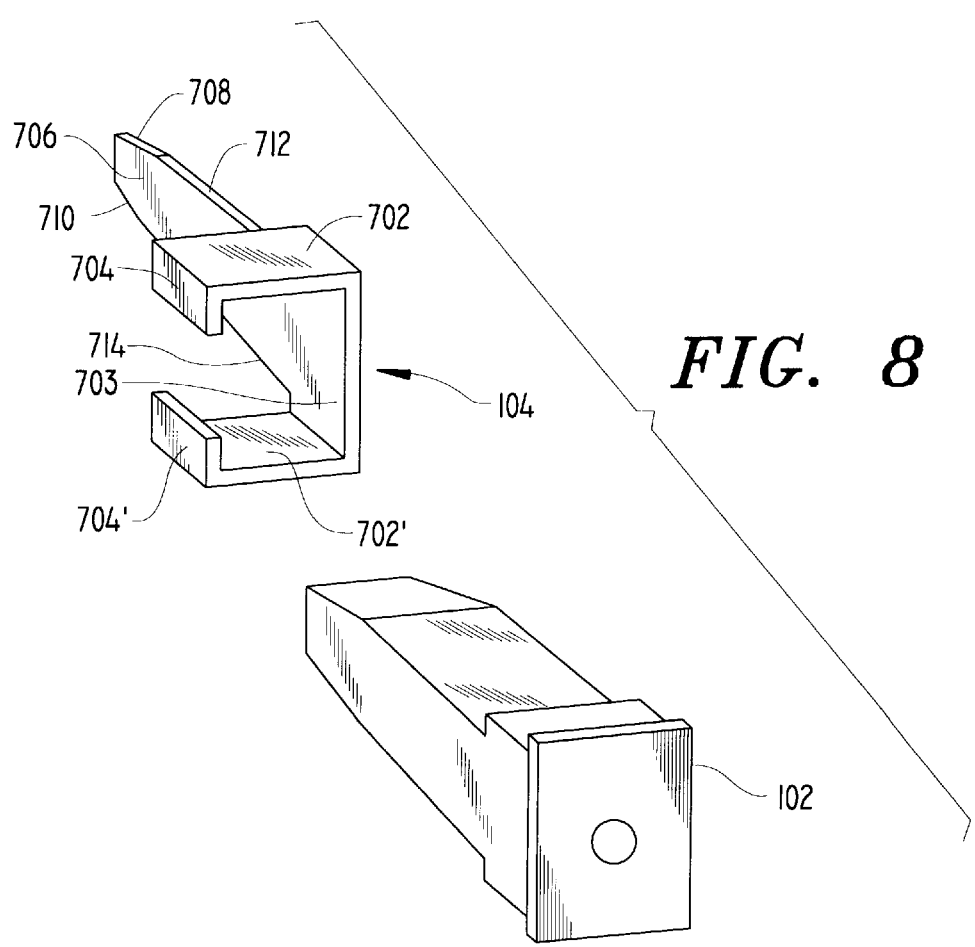
FIG. 8 is an exploded perspective view of a wedge-channel device designed for bilateral insertion about the spinal column.

FIG. 8 depicts a particular embodiment wherein the distractor channel defining means is designed for bilateral insertion on one or more sides about the spinal column. In this embodiment, channel defining means 104 is illustrated as having a proximal end including substantially parallel end walls 702, 702' which are in spaced apart relation from a basewall 703 extending therebetween, and a pair of enclosing walls 704, 704' disposed substantially perpendicular to said endwalls and in spaced relation to said basewall. The channel defining means is further defined by a distal end including a wedge-shaped wall member 706 extending from said proximal end and further includes pairs of coplanar edges in converging relationship 708, 710 and 712, 714, defining one or more angles of convergence. The edges are effective to maintain a particular intervertebral space after slidable disengagement of wedge 102, thereby defining a convenient access port within the intervertebral space. This embodiment is particularly well suited for an anterior approach where delicate soft tissue structure makes use of the embodiment defined by FIG. 1 difficult.

It is to be understood that while a certain form of the invention is illustrated, it is not to be limited to the form or arrangement of parts herein described and shown. It will be apparent to those skilled in the art that various changes may be made without departing from the scope of the invention and the invention is not to be considered limited to what is shown and described in the specification and drawings.

What is claimed is:

1. A combined wedge and channel intervertebral distraction device for producing and maintaining an intervertebral access port between adjacent vertebral end plates comprising:

channel defining means adapted for placement between adjacent vertebral end plates;

wedge means adapted for insertion within said channel defining means; and impactor means, releasably coupled with said wedge, said impactor means constructed and arranged to facilitate positioning between adjacent vertebral end plates;

wherein positioning said wedge and channel distraction device between said adjacent vertebral end plates creates an intervertebral space, said space being accessible upon removal of said wedge means.

2. The combined wedge and channel intervertebral distraction device in accordance with claim 1 wherein said channel defining means includes a proximal end and a distal end, said proximal end including a pair of substantially parallel endwalls spaced apart by a basewall extending therebetween, and a pair of enclosing walls disposed substantially perpendicular to said endwalls and in spaced relation to said basewall;

said channel defining means distal end including at least one wedge-shaped wall member extending from said proximal end and including coplanar edges in converging relationship, said edges being effective to maintain a particular intervertebral space;

wherein said channel defining means is adapted for slidable engagement of said wedge means therein.

3. The combined wedge and channel intervertebral distraction device in accordance with claim 2 wherein said coplanar edges define an angle of convergence of from about 2 degrees to about 15 degrees.

4. The combined wedge and channel intervertebral distraction device in accordance with claim 1 wherein said wedge means includes a lower surface, an upper surface and opposing side surfaces, said wedge means dimensioned for slidable insertion within said channel defining means;

a distracting surface for opening the intervertebral space; and an impact surface adapted to mechanically engage said impactor means;

wherein a force exerted on said wedge by said impactor means urges the distracting surface within the intervertebral space.

5. The combined wedge and channel intervertebral distraction device in accordance with claim 4 wherein said opposing side surfaces form a continuous wall therebetween.

6. The combined wedge and channel intervertebral distraction device in accordance with claim 5 wherein said continuous wall includes cascading ridges which ridges define decortication cutting edges.

7. The combined wedge and channel intervertebral distraction device in accordance with claim 5 wherein said continuous wall includes a centrally disposed passage.

8. The combined wedge and channel intervertebral distraction device in accordance with claim 1 wherein said device is constructed from titanium or an alloy thereof.

9. The combined wedge and channel intervertebral distraction device in accordance with claim 1 wherein a distal end of said channel defining means includes at least two wedge-shaped wall members adapted to define outer boundaries of said intervertebral space.

10. A combined channel defining means and retractor for producing and maintaining an intervertebral portal between adjacent vertebral end plates comprising:

an elongated tubular structure having a proximal end and a distal end, said tubular structure having at least one bore therein, said distal end having a groove there across defined by parallel upstanding sidewalls;

said channel defining means having a proximal end and a distal end, said proximal end including a pair of substantially parallel endwalls spaced apart by a basewall extending therebetween, and a pair of enclosing walls disposed substantially perpendicular to said endwalls and in spaced relation to said basewall;

said channel defining means distal end including at least one wedge-shaped wall member extending from said proximal end and including coplanar edges in converging relationship, said edges being effective to maintain a particular intervertebral space;

wherein said proximal end of said channel defining means is disposed in said groove in said tubular structure.

11. A combined channel defining means and retractor in accordance with claim 10 wherein said tubular structure has at least two bores therein.

* * * * *